US011344507B2

(12) United States Patent
Utecht et al.

(10) Patent No.: US 11,344,507 B2
(45) Date of Patent: May 31, 2022

(54) TOPICAL COMPOSITIONS CONTAINING LOW MOLECULAR WEIGHT CHITOSAN DERIVATIVES

(71) Applicants: ALUMEND, LLC, Sioux Falls, SD (US); WAVEPHARMA, LLC, New Orleans, LA (US)

(72) Inventors: Ronald E. Utecht, Volga, SD (US); Rachel Gyasi, Sioux Falls, SD (US); Miri Seiberg, Princeton, NJ (US)

(73) Assignees: Alumend, LLC, Sioux Falls, SD (US); WavePharma, LLC, New Orleans, LA (US)

( * ) Notice: Subject to any disclaimer, the term of this patent is extended or adjusted under 35 U.S.C. 154(b) by 0 days.

(21) Appl. No.: 16/736,643

(22) Filed: Jan. 7, 2020

(65) Prior Publication Data

US 2020/0281869 A1 Sep. 10, 2020

Related U.S. Application Data

(60) Provisional application No. 62/789,599, filed on Jan. 8, 2019.

(51) Int. Cl.
*A61K 31/07* (2006.01)
*A61K 8/73* (2006.01)
*A61K 8/06* (2006.01)
*A61K 8/35* (2006.01)
*A61K 9/00* (2006.01)
*A61K 9/107* (2006.01)
*A61K 31/216* (2006.01)
*A61K 47/36* (2006.01)
*A61Q 17/04* (2006.01)

(52) U.S. Cl.
CPC .............. *A61K 31/07* (2013.01); *A61K 8/06* (2013.01); *A61K 8/35* (2013.01); *A61K 8/736* (2013.01); *A61K 9/0014* (2013.01); *A61K 9/107* (2013.01); *A61K 31/216* (2013.01); *A61K 47/36* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 4,385,049 A * | 5/1983 | Cuca | A61K 8/06 514/777 |
| 5,422,116 A | 6/1995 | Fen et al. | |
| 5,496,872 A | 3/1996 | Constancis et al. | |
| 5,773,033 A | 6/1998 | Cochrum et al. | |
| 6,200,595 B1 | 3/2001 | Motoyashiki et al. | |
| 6,310,188 B1 | 10/2001 | Mukherjee | |
| 6,329,337 B1 | 12/2001 | Morita et al. | |
| 6,541,773 B1 | 4/2003 | Iwabuchi et al. | |
| 6,875,796 B2 | 4/2005 | Stedronsky | |
| 6,991,652 B2 | 1/2006 | Burg | |
| 7,514,399 B2 | 4/2009 | Utecht et al. | |
| 7,666,859 B2 | 2/2010 | Turkowitz | |
| 9,833,469 B2 | 12/2017 | Utecht et al. | |
| 9,884,121 B2 | 2/2018 | Utecht et al. | |
| 2002/0172672 A1 | 11/2002 | Seiberg et al. | |
| 2003/0157035 A1 | 8/2003 | Chaudhuri | |
| 2003/0206958 A1 | 11/2003 | Cattaneo et al. | |
| 2004/0047892 A1 | 3/2004 | Desrosiers et al. | |
| 2005/0113288 A1 | 5/2005 | Utecht et al. | |
| 2005/0283004 A1 | 12/2005 | Wei et al. | |
| 2006/0013885 A1 | 1/2006 | Nah et al. | |
| 2007/0269534 A1 | 11/2007 | Ramirez et al. | |
| 2008/0200948 A1 | 8/2008 | Utecht et al. | |
| 2014/0330005 A1 * | 11/2014 | Gao | A61K 31/11 536/123.1 |
| 2017/0182086 A1 | 6/2017 | Utecht et al. | |

FOREIGN PATENT DOCUMENTS

| | | |
|---|---|---|
| WO | 1992009636 A1 | 6/1992 |
| WO | 2001045645 A1 | 6/2001 |
| WO | 2005044309 A1 | 5/2005 |
| WO | 2005113608 A1 | 12/2005 |
| WO | 2008094675 A2 | 8/2008 |

OTHER PUBLICATIONS

International Search Report and Written Opinion issued in PCT/US2020/012539 dated Apr. 9, 2020.
Aranaz et al. 'Functional Characterization of Chitin and Chitosan' Current Chemical Biology, vol. 3, No. 2, pp. 203-230 (28) 2009.
Kumar et al. 'Recent Developments in Phase Inversion Emulsification' Ind. Eng. Chem. Res. 54, 34, 8375-8396, 2015.
Kumar M., A Review of Chitin and Chitosan Applications. Reactive and Functional Polymers, 46:1-27, 2000.
Park, J. et al. Synthesis and Characterization of Sugar-Bearing Chitosan Derivatives: Aqueous Solubility and Biodegradability Biomacromolecules, 2003, 4:1087-91.
International Search Report and Written Opinion issued in International Application No. PCT/US2016/068060 dated Feb. 24, 2017.
Kim, "Safety Evaluation and Anti-wrinkle Effects of retinoids on Skin", Toxicol. Res. vol. 26, No. 1, 61-66, 2010.

(Continued)

*Primary Examiner* — Jennifer A Berrios

(74) *Attorney, Agent, or Firm* — Burns & Levinson, LLP; Shawn P. Foley

(57) ABSTRACT

Disclosed are topical composition for delivery of an active agent to keratinous tissue, comprising a low molecular weight chitosan that is covalently modified chitosan with octane sulfonic acid which are attached to the chitosan via sulfonamide linkages (OsC), an effective amount of an active agent, and a carrier, and wherein the chitosan has a molecular weight of about 50 kD to about 150 kD. Also disclosed are methods of making the compositions and methods of using the compositions that entail topical application.

20 Claims, No Drawings

(56) References Cited

OTHER PUBLICATIONS

"Aqueous cream: may cause skin irritation"; Mar. 25, 2013, retrieved from https://www.gov.uk/drug-safety-update/aqueous-cream-may-cause-skin irritation.
WebMD ("Hydrocortisone Antipruritic Cream Side Effects by Likelihood and Severity", retrieved from https://www.webmd.com/drugs/2/drug-61546/hydrocortisone-antipruritic-topi- cal/details/list-sideeffects on Feb. 6, 2018.
Contact Dermatitis. Encyclopedia of Children's Health. Mar. 19, 2011.
Ngan. "Sunscreen allergy." DermNet NZ. (2012). Retrieved Mar. 28, 2018.

* cited by examiner

TOPICAL COMPOSITIONS CONTAINING LOW MOLECULAR WEIGHT CHITOSAN DERIVATIVES

This application claims benefit of U.S. Provisional Application No. 62/789,599, filed Jan. 8, 2019, the disclosures of which are incorporated herein by reference in their entireties of all purposes.

BACKGROUND

The topical treatment of skin ailments have been long associated with the side effect of increased irritation. For example, topical retinoids have been extensively used to treat numerous skin disorders, including acne, psoriasis, skin aging, and certain types of cancers. However, irritant reactions such as burning, scaling or dermatitis associated with retinoid therapy markedly limit their acceptance by patients and consumers. As reviewed in Mukherjee, et al., Clin. Interv. Aging 1(4): 327-48 (2006), various solutions have been developed to reduce retinoid irritation, including the reduction in concentration and dosing frequency, the development of retinoid derivatives that are less irritating, the combination with anti-inflammatory agents (e.g., hydrocortisone) and the creation of novel delivery systems (e.g., nanoparticles, liposomes). Unfortunately, even retinol, which is among the milder retinoids, induces significant irritation and cannot be tolerated by many individuals.

Efforts to reduce retinoid irritation are ongoing, including e.g., encapsulation, polymer use for controlled release, the combination with steroids, and the like. See, e.g., Shields, et al., J. Control Release 28:278:37-48 (2018) (encapsulation and controlled release of retinol from silicone particles for topical delivery); Castleberry, et al., J. Control Release. 28(262):1-9 (2017) (polymer conjugated retinoids for controlled transdermal delivery); and Coman, et al., Br. J. Dermatol. 177(2):567-569 (2017) (reporting a randomized, split-face, controlled, double-blind, single-centre clinical study: transient addition of a topical corticosteroid to a topical retinoid in patients with acne to reduce initial irritation).

One approach to alleviate skin irritation associated with topical application of various agents involving formulating them in high molecular weight (e.g., 360,000-400,000 daltons) synthetic and non-biodegradable polymers. However, concerns were raised about the safety of these formulations in view of the non-biodegradability of the synthetic polymers. See, U.S. Patent Application Publication 2003/0206958 A1, and publications cited therein.

Subsequent attempts have focused on use of biodegradable polymers, including chitin and especially its water-soluble derivative chitosan. Next to cellulose, chitin is the most abundant polysaccharide on earth. It is found in hard structures and strong materials in which it functions as a reinforcement bar. Together with calcium salts, some proteins and lipids, chitin builds up the exoskeletons of marine organisms like crustaceans and arthropods. It is also found in the cell walls of some bacteria, sponges and fungi and in the build-up of the hard shells and wings of insects. Commercially, chitin is isolated mainly from crustacean shells, which is a waste product from the fish industry. Chitin is not water soluble, which strongly limits its use. However, treatment of chitin with strong alkali yields a partly deacetylated and water-soluble derivative chitosan. Chitosan is a linear polysaccharide composed of 1,4-beta-linked D-glucosamine and N-acetyl-D-glucosamine residues. See, generally, Dunn, et al., J. Bioact. & Compat. Poly. 7:370-97 (1992).

U.S. Patent Application Publication 2003/0206958 A1 teaches topical compositions wherein active agents such as retinoids are formulated with a carrier that includes a high viscosity and high molecular weight chitosan. The '958 Publication teaches that the molecular weight of the chitosan is preferably at least about 100,000 daltons (i.e., 200 kilo-Dalton (kD)), more preferably at least about 250,000 daltons and most preferably at least about 300,000 daltons. In certain of these embodiments, the chitosan is present in a concentration greater than about 2%. According to the '958 Publication, these compositions are especially useful for obtaining slow, sustained release of the active agent, which reduces irritation caused by agents such as retinoids. U.S. Pat. No. 9,884,121 to Utecht et al., teaches treated and/or modified chitosans, including chitosans covalently modified by octane sulfonic acid groups attached to the chitosan via sulfonamide linkages ("OsC") for a variety of uses including drug delivery, and as an adhesive, filler and bulking agent. The disclosed molecular weights of the OsC's range from about 219,000 to about 260,000 daltons (as determined by size exclusion chromatography with multi-angle light scattering (MALS) detection). U.S. Pat. No. 9,833,469, also to Utecht, et al., teaches use of modified chitosans, including OsC, as a topical delivery vehicle for agents known to cause skin irritation.

SUMMARY OF THE INVENTION

Contrary to teachings in the art that higher molecular weight chitosan is more desirable or preferred for purposes of formulating skin irritants such as retinoids, the present applicant has surprisingly and unexpectedly discovered that compositions containing a skin irritant and a carrier base that includes chitosan having a molecular weight of about 50 to about 150 kilodaltons (kD) and which is covalently modified with octane sulfonic acid groups attached to the chitosan via sulfonamide linkages ("OsC"), exhibit even less skin irritation as compared to octane sulfonic acid-modified chitosans having molecular weights outside this range.

Applicant has also surprisingly and unexpectedly discovered the compositions containing an active agent and the low molecular weight covalently modified chitosan exhibit similar skin retention properties while improving upon the reduction in irritation, as compared to compositions containing high molecular weight covalently modified chitosans. That is, the retention time of the active agent on the skin is about the same as the retention time following application of a non-inventive composition containing a higher molecular weight covalently modified chitosan but skin irritation is further reduced relative to the non-inventive composition.

Thus, compositions of the present invention provide unexpected improvements in the art with respect to topically applied active agents, by enhancing retention time and reducing skin irritation that is caused by some active agents.

Accordingly, a first aspect of the present invention is directed to a composition for the topical delivery of an active agent that includes an effective amount of an active agent and the carrier base. In some embodiments, the active agent is a pharmaceutically active agent. In some other embodiments, the active agent is a cosmetically or therapeutically active agent. In some embodiments, the active agent causes skin irritation. Methods of making the compositions are also provided.

A second aspect of the present invention is directed to a method of treating keratinous tissue that entails topically applying a composition of the present invention to the tissue.

DETAILED DESCRIPTION OF THE INVENTION

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Octane Sulfonic Acid Modified Low Molecular Weight Chitosan

The present invention utilizes chitosan having a molecular weight (MW) of about 50 to about 150 kD. MW may be measured by as determined by size exclusion chromatography with multi-angle light scattering (MALS) detection. Chitosan having a molecular weight in the range of from about 50 kD to about 150 kD can be made via known techniques or is other available commercially from numerous suppliers. The original source of the chitosan, e.g., animal or non-animal, is not critical for purposes of the present invention. In some embodiments, the chitosan has a molecular weight of from about 50 kD to about 100 kD. In some embodiments, the chitosan has a molecular weight of from about 50 kD to about 80 kD. In some embodiments, the chitosan has a molecular weight of about 50 kD, i.e., from 40-60 kD. Modification of the chitosan with octane sulfonic acid groups (which are linked to the chitosan backbone via sulfonamide linkages) in accordance with methods known in the art, such as for example, those described in U.S. Pat. No. 9,884,121, to Utecht, et al.

Compositions of the present invention include sulfonamide linkages (OsC) in amounts that generally vary from about 0.0001-5% W/V, based on the total weight of the composition. In some embodiments, the OsC may vary from about 0.001% W/V to about 3% W/V, based on the total weight of the topical composition. In yet other embodiments, the OsC may vary from about 0.5% W/V to about 2.0% W/V, based on the total weight of the topical composition.

Active Agents

Active agents are any agent that is known to produce a desired effect upon topical application to keratinous tissue (hair, scalp, nails and skin) of a human or animal, and may thus include pharmaceutical actives and therapeutic or cosmetic actives alike, as well as any other agent that may provide some beneficial effect when topically applied.

Pharmaceutical actives are those used for the treatment of skin diseases. Representative types of such agents include retinoids, anti-bacterial agents (e.g., antibiotics), anti-viral agents, anti-parasitic agents (e.g., ivermectin), anti-wart agents, anti-fungal agents, anti-inflammatory agents such as corticosteroids and non-steroidal anti-inflammatory drugs (NSAIDS), antibiotics, antiseptics, local anaesthetics, pharmaceutically active peptides, actinic keratosis treatments (e.g., 5-fluoro-uracil or imiquimod), rosacea treatments (e.g., azaleic acid and metronidazole), psoriasis treatments, wound treatments, analgesics, acne therapeutic agents (e.g., salicylic acid and benzoyl peroxide), rosacea therapeutic agents and vitamins and derivatives thereof.

As is known in the art, cosmetic agents are used for cleansing, beautifying, promoting attractiveness, or altering the appearance (e.g., "anti-aging" products), representative examples of which include cosmetic products (e.g., beautifying products and ingredients contained therein) such as skin care products (e.g., moisturizers), perfumes, lipsticks, eye shadow, color-corrector, rouge, eye-liner, mascara fingernail polishes and removers, eye and facial makeup preparations, shampoos, permanent waves, hair colors, toothpastes, anti-perspirants and deodorants, fragrances, sunscreens (also referred to herein as photoprotectants), sunless tanning agents, depilatory agents, hair growth agents such as minoxidil, hair removal agents, dandruff control agents, shaving and after-shaving agents, colorants (e.g., dyes and pigments), lightening agents, darkening agents, beautifying agents (e.g., lipstick and the like), chemical peels, anti-oxidants, vitamins and natural (e.g., botanical) extracts.

Yet other types of active agents that may be formulated with the OsC for topical application include cleansing agents, soaps and detergents (e.g., sodium hydroxide, which is found, e.g., in soaps, detergents, cleaning products, adhesives, paint removers and disinfectants, and sodium dodecyl sulfate, also known as sodium lauryl sulfate (SLS), which is used in cleaning and personal hygiene products), insecticides, paint removers, solvents found, e.g., in paint removers, nail polish removers and topical alcohol products, adhesives, preservatives, transdermal-delivery agents and devices, acids, bases, and minerals.

In some embodiments, the active agent is a retinoid. Retinoids are a class of natural and synthetic compounds alike that include vitamin A (also known as retinol) and its related chemicals or derivatives. Retinoids like retinoic acid, retinol (and vitamin A precursors), and their derivatives are used in numerous pharmaceutical and skin care products, and serve as the "gold standard" active ingredients for "anti-aging" skin care and for treatment of acne. Retinoids affect the dermis, the epidermis and skin appendices, enhance skin health and wellness, decrease fine lines, even skin color, improve texture, tighten pores, and stimulate blood flow and collagen production. Retinoids are also very effective anti-acne compounds and have been shown to have efficacy in treating psoriasis.

Representative examples of retinoids include retinol, retinoic acid, retinaldehyde (also known as retinal), esters of retinol or of retinoic acid (tretinoin), including, e.g., retinyl palmitate, retinyl acetate, retinyl propionate, retinyl butyrate, retinyl hexanoate, retinyl heptanoate, retinyl caprylate, and retinyl stearate, and synthetic retinoids such as tocopheryl-retinoate (tocopherol ester of retinoic acid (transor cis-)), adapalene, bexarotene, and tazarotene. In some embodiments, the retinoid is all trans-retinol or 13-cis-retinoic acid (i.e., isotretinoin which is commercially marketed under the tradename ACCUTANE®), 9-cis-retinoic acid (i.e., alitretinoin which is marketed under the tradename PANRETIN®), etretinate (marketed in Japan under the tradename TIGASON) and acitretin (marketed under the tradenames SORIATANE® and NEOTIGASON®). These compounds are well known in the art and are commercially available from a number of sources, e.g., Sigma Chemical Company (St. Louis, Mo.), Boerhinger Mannheim (Indianapolis, Ind.), BASF (Mt. Olive, N.J.), and Roche (Basel, Switzerland).

The retinoids, as any topical agents embraced by the present invention, are present in the compositions in an "effective amount" which to impart their intended function when applied. In the context of retinoids, the term "effective amount" refers to an amount that is sufficient to significantly induce a positive benefit to keratinous tissue, such as a health, appearance, and/or feel benefit, including, independently or in combination, the benefits disclosed herein, but low enough to avoid serious side effects (i.e., to provide a reasonable benefit to risk ratio, within the scope of sound judgment of the skilled artisan). An effective amount of a retinoid is an amount of sufficient to regulate a desired condition of mammalian keratinous tissue when topically applied thereto in a personal care composition over the course of a treatment period. The specific amounts/concentrations of the retinoid in the compositions may depend on one or more factors such as the type of the retinoid, the specific activity of the retinoid, the desired biological effect of the retinoid, the profile of side effects of the retinoid, the age, gender, skin type and the body site of the treated skin.

The compositions of the invention may be formulated with an amount of a retinoid that generally varies from about 0.001 to about 5% W/V, based on the total weight of the composition. In other embodiments, the composition may be formulated with an amount of a retinoid that is from about 0.01-1% W/V, based on the total weight of the composition. In yet other embodiments, the composition may be formulated with an amount of a retinoid that varies from 0.04-0.5% W/V, based on the total weight of the composition.

Sunscreen agents (also known as photo-protective agents, photoprotectants and U.V. absorbers or filters) include both organic and inorganic (or physical) agents. Representative examples of organic sunscreen agents that may be suitable for use in the present invention include dibenzoylmethane derivatives (e.g., butylmethoxydibenzoylmethane); cinnamic derivatives (e.g., ethylhexyl methoxycinnamate, isopropyl methoxycinnamate, isoamyl methoxycinnamate, N,N-diethylaniline (DEA) methoxycinnamate, diisopropyl methylcinnamate, and glyceryl ethylhexanoate dimethoxycinnamate); para-aminobenzoic acid (PABA) and derivatives (e.g., ethyl PABA, ethyl dihydroxypropyl PABA, ethylhexyl dimethyl PABA, glyceryl PABA, and PEG-25 PABA); salicylic derivatives (e.g., homosalate, ethylhexyl salicylate, dipropyleneglycol salicylate, and TEA salicylate); (3-diphenylacrylate derivatives (e.g., octocrylene and etocrylene); benzylidenecamphor derivatives (e.g., 3-benzylidene camphor, 0.4-methylbenzylidene camphor, benzylidene camphor sulfonic acid, camphor benzalkonium methosulfate, terephthalylidene dicamphor sulfonic acid, and polyacrylamidomethyl benzylidene camphor; phenylbenzimidazole derivatives (e.g., phenylbenzimidazole sulfonic acid, and disodium phenyl dibenzimidazole tetrasulfonate); phenylbenzotriazole derivatives (e.g., drometrizole trisiloxane and methylene bis-benzotriazolyl tetramethylbutyl-phenol); triazine derivatives (e.g., bis-ethylhexyloxyphenol methoxyphenyl triazine, ethylhexyl triazone, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis(n-butyl 4'-aminobenzoate)-6-(aminopropyl-trisiloxane)-s-triazine, and 2,4-bis(dineopentyl 4'-aminobenzalmalonate)-6-(n-butyl 4'-aminobenzoate)-s-triazine); anthranilic derivatives (e.g., menthyl anthranilate); imidazoline derivatives (e.g., ethylhexyl dimethoxybenzylidene dioxoimidazoline propionate); benzalmalonate derivatives (e.g., polyorganosiloxane comprising benzalmalonate functional groups); 4,4-diarylbutadiene derivatives (e.g., 1,1-dicarboxy(2,2'-dimethylpropyl)-4,4-diphenylbutadiene); benzoxazole derivatives (e.g., 2,4-bis[5-1-(dimethylpropyl)benzoxazol-2-yl-(4-phenyl) imino]-6-(2-ethylhexyl)imino-1,3,5-triazine); and merocyanine derivatives (e.g., octyl 5-(N,N-diethylamino)-2-phenylsulfonyl-2,4-pentadienoate).

In some embodiments, the organic sunscreen agent is octocrylene (also known as ethylhexyl methoxycinnamate, commercially available under the tradename OCTINOXATE), octyl methoxycinnamate (commercially available under the tradenames EUSOLEX® 2292 and UVINUL® MC80, homosalate, octisalate, octinoxate, avobenzone, and oxybenzone, and combinations of two or more thereof.

Representative inorganic photoprotectants are typically pigments formed of metal oxides which may or may not be coated (and which typically have a mean particle size between about $5 \times 10^{-3}$ µm and $100 \times 10^{-3}$ µm. Specific examples include pigments formed of titanium oxide, iron oxide, zinc oxide, zirconium oxide, and cerium oxide. In some embodiments, the inorganic sunscreen agent is $TiO_2$ or $ZnO_2$ or a combination thereof.

Yet other representative examples of organic and inorganic photoprotective agents that may be useful in the present invention are disclosed, for example, U.S. Patent Application Publication 2010/0190740 A1.

Sunscreen agents are generally present in an amount ranging from about 0.5% to about 50%, and in some embodiments from about 1% to about 40% by weight, based on the total weight of the composition.

Representative examples of vitamins include Vitamin A (i.e., retinol) and its related chemicals and derivatives (as described above), tocopherols (e.g., alpha-tocopherol (Vitamin E)), 7-dehydrocholesterol (Vitamin D), Vitamin K, thiamine riboflavin, niacin, pyridoxine, biotin, pantothenic acid, ascorbic acid, choline and inositol, and their derivatives that are known to be effective when applied topically.

Representative examples of skin care (e.g., moisturizing agents) include lactic acid, pyrrolidone carboxylic acid, glycolic acid, water, glycerin, propylene glycol, sorbitol, and alpha-hydroxy carboxylic acids. This class of actives may also include percutaneous absorption enhancers such as urea, diethyl sebecate, sodium lauryl sulfate, sodium laureth sulfate, sorbitan ethoxylates, nicotinate esters (such as hexyl nicotinate), oleic acid, pyrrolidone carboxylate esters (such as dodecyl pyrrolidone carboxylate), N-methyl pyrrolidone, N,N-diethyl-mtoluamide, dimethyl sulfoxide, decyl methyl sulfoxide, alkyl methyl sulfoxides, N,N-dimethyl formamide, cis-11-octadecenoic acid, 1-dodecylazacycloheptan-2-one, and 1,3-dioxacyclopentane or 1,2-dioxacyclohexane containing at least one aliphatic group 4-18 carbon atoms.

In some embodiments, the active agent is known to cause skin irritation. Skin irritation results in a rash, which is a visible change in the color or texture of the skin. Irritated skin may become red, itchy, bumpy, chapped, or flaky, with hives. IL-1α (interleukin-1α, also named IL-1α), is an inflammatory cytokine that serves as a biomarker for skin irritation. Topical agents that cause skin irritation, e.g., sodium dodecyl sulfate (SDS) and retinoids, are known to induce IL-1α secretion in a dose-responsive manner. Reduction in IL-1α secretion have been shown to correlate with a reduction or amelioration of topical agent-induced skin irritation. See, U.S. Pat. No. 9,833,469, to Utecht, et al.

Representative examples of active agents that are known to cause skin irritation include dermatological agents are disclosed hereinabove, e.g., retinoids, chemical peels, anti-oxidants, salicylic acid, benzoyl peroxide, actinic keratosis treatments such as 5-fluoro-uracil and imiquimod, rosacea treatments such as azaleic acid and metronidazole, psoriasis treatments, wound treatments, wart treatments, steroids, non-steroidal anti-inflammatory agents, analgesics, cleansing agents (e.g., soaps and detergents such as those that include sodium hydroxide and harsh surfactants such as SDS), disinfectants (such as those that include potassium hydroxide), antiseptics, deodorants and antiperspirants, insecticides, fragrances, colorants, sunscreens, depilatory agents, hair growth agents such as minoxidil, dandruff control agents, after-shaving agents, solvents (such as those used in paint removers, nail polish removers, and topical alcohol products), adhesives, preservatives, transdermal-delivery agents and devices, acids, bases, and minerals.

In general, the amount of active employed will be that amount necessary to deliver a pharmaceutically or therapeutically effective amount to achieve the desired result at the site of application. In practice, this will vary depending upon the particular medicament, severity of the condition as well as other factors. In general, the concentration of the actives in the delivery systems can vary from as little as 0.0001 up to about 40 percent or higher, by weight of the delivery system.

Main Types of Cosmetic Compositions

Broadly, cosmetic compositions in which the active agents may be formulated fall into three general categories, namely: anhydrous-based compositions; aqueous-based compositions wherein water is present as a major ingredient; and multiphasic compositions or emulsions, that include two or more phases that are aqueous and oil-based, wherein the discrete (e.g., continuous and discontinuous) phases are dispersible by the presence of an emulsifier or other cosmetic ingredient with emulsifying properties. Examples of emulsions include water-in-oil, water-in-oil-in-water, oil-in-water, silicone-in-water, water-in-silicone, oil-in-water-in-oil, and oil-in-water-in-silicone emulsions. Accordingly, compositions of the present invention may be solid, semi-solid or liquid, and may thus be formulated as solutions, suspensions, emulsions, lotions, creams, gels, drops, sticks, sprays, ointments, cleansing liquids, washes, solid bars, shampoos, hair conditioners, hair colorants, pastes, foams, powders, mousses, shaving creams, shaving gels, wipes, patches, hydrogels, film-forming products, masks, liquid drops, muco-adhesives, nail polishes and nail gels.

The pH of the compositions is not critical. In some embodiments, the compositions are formulated to have a pH in the range of about 4.5 to about 7.5, and in some other embodiments, from about 5 to about 6. Inclusion of pH adjusting agents/buffering agents will suffice for this purpose.

The invention will now be described in terms of the following illustrative and non-limiting working examples.

Example 1: Preparation of Chitosans Covalently Modified with Octane Sulfonic Acid Using Different Molecular Weight Chitosans Chitosans covalently modified with octane sulfonic acid (OsC) were prepared according to U.S. Pat. Nos. 9,884,121 and 9,855,337.

In a beaker, 2 grams of chitosan were combined with 40 mL of 10% (v/v) lactic acid. The chitosan was allowed to solubilize overnight. When the chitosan was fully dissolved the sample was placed on a mechanical mixer and stirred at a speed of 80-120 rpm and allowed to mix for 30 minutes. With continued mixing, 100 µL of octanesulfonyl chloride was added dropwise to the chitosan. The sample was allowed to mix for an hour and then 6M NaOH was slowly added until the pH of the sample was between 9 and 10. This pH was maintained with continued mixing for 2 hours. The chitosan was then redissolved by the addition of 100 mL of 10% (v/v) lactic acid. When all of the modified chitosan was dissolved the sample was reprecipitated by the slow addition of 6M NaOH. Mixing was terminated and the sample was divided equally among 4 centrifuge tubes (50 mL) and the samples centrifuged at a sufficient speed and time to sediment out the chitosan. Generally, sedimentation is conducted at about 3850.times.G. The supernatant was discarded and the modified chitosan placed into dialysis tubing. The chitosan was then dialyzed with 10% (v/v) lactic acid until all of the chitosan was dissolved. The acid dialysate was then removed and replaced with deionized water and dialyzed for no less than 3 hours. The deionized water was then replaced 2 additional times for a total of 3 water washes. A small aliquot of chitosan was removed from the dialysis tubing and a pH measurement was made. The dialysate was then changed to PBS pH 7.4 and the dialysis was monitored until the pH of the chitosan was in the range of 5.7 to 6.0. The chitosan was then dialyzed three times against deionized water with each wash lasting no less than 3 hours. The chitosan then went through the freeze-drying, reconstitution and sterilization steps outlined above. The desired final pH of the formulation was 6.2 to 6.4.

Different chitosans, of different sources and molecular weights (MW), were used to prepare the OsCs, as described in Tables 1a and 1b, below. The molecular weight of the chitosan source was found to correlate with physical properties of the related OsC. In most cases, the lower MW OsC was easier to solubilize, and did not require heating.

TABLE 1a

| OsC type | Chitosan source | Chitosan Molecular Weight (kD) | Solubility (1% in PBS) | Appearance (1% in PBS) |
| --- | --- | --- | --- | --- |
| TFF OsC | Shrimp | 725 ± 32 | Requires heat to fully solubilize | Slightly viscous, colorless solution |
| OcC50 | Mushroom | 50 ± 10 | Fully soluble without heat | Minimally viscous, amber-tinted solution |
| OcC150 | Mushroom | 150 ± 10 | Fully soluble without heat | Minimally viscous, amber-tinted solution |
| OcC300 | Mushroom | 300 ± 10 | Requires heat to fully solubilize | Slightly viscous, colorless solution |

TABLE 1b

| OsC type | Chitosan source | Chitosan Molecular Weight (kD) | Solubility (1% in PBS) | Appearance (1% in PBS) |
| --- | --- | --- | --- | --- |
| OmyC25 | Fungal | 25 ± 10 | Fully soluble without heat, falls out of solution over time | Minimally viscous, cloudy solution |

TABLE 1b-continued

| OsC type | Chitosan source | Chitosan Molecular Weight (kD) | Solubility (1% in PBS) | Appearance (1% in PBS) |
|---|---|---|---|---|
| OmyC140 | Fungal | 140 ± 10 | Requires heat to solubilize, contains undissolved solids | Minimally viscous, cloudy solution |
| OmyC340 | Fungal | 340 ± 10 | Requires heat to solubilize, contains undissolved solids | Minimally viscous, light yellow solution |
| OkgC | *Aspergillus niger* | 15 ± 10 | Solubilizes without heat, contains undissolved fine solids | Minimally viscous, light brown solution |
| OkhC | *Aspergillus bisporus* | 80 ± 10 | Requires heat to fully solubilize | Slightly viscous, colorless solution |
| ObondC80 | *Pleurotus ostreatus* | Unknown | Requires heat to solubilize, contains undissolved solids | Minimally viscous, colorless solution |
| ObondC600 | *Pleurotus ostreatus* | 353 ± 10 | Requires heat to fully solubilize, contains undissolved solids | Minimally viscous, colorless solution |

Example 2: SDS-Induced Irritation

An in vitro Skin Irritation Test was performed according to OCED guidelines. Irritant materials are identified by their ability to decrease cell viability below a defined threshold level of 50%. Moreover, if the cytotoxic effect is absent or weak, a quantifiable amount of inflammatory mediators (e.g., IL-1α) is released by the epidermis and may be used in a tiered approach to increase the sensitivity of the test.

OsCs (30 µl) were topically applied onto three-dimensional human epidermal equivalents (EPI-200 from MatTek, Ashland, Mass.), n=3 tissues per treatment group. When dried, SDS was applied to the tissues as described in Table 2. Test materials included a positive control irritant (5% sodium dodecyl sulfate, SDS), and a negative control (Phosphate Buffered Saline, PBS), and aqueous SDS solutions of 0.2, 0.4 and 0.6%, with or without the addition of different OsCs (1%) as described in Table 1a. The OsCs (1%) alone were also included.

After 60-minute exposure, the tissues were rinsed with PBS and were transferred to fresh medium. After 24 hours, media was collected for IL-1α analysis. Tissues were then transferred to fresh media for an additional 18 hr to allow the toxic effect of irritant chemicals to develop. After the 42 hr post-exposure equilibration, media was again collected and tissue viability was determined using an 3-(4,5-dimethylthiazol-2-yl)-2,5-diphenyltetrazolium bromide (MTT) assay. The results of this study are shown in Table 2.

The MTT assay cut-off is 50%, defining agents that result in less than 50% viability as irritants. As shown by the MTT assay (Table 2), increasing concentrations of SDS result in an increase loss of cell viability, with at 0.6% SDS resulting in 19.21% viability (defined as an irritant), while each OsC alone (at 1%) is defined as a non-irritant. Combining Each OsC with the increasing SDS concentration significantly improved cell viability at all SDS concentrations, an even enhanced it to >100% in most cases. Using the viability criteria alone, the combination of OsC with 0.6% SDS would be defined as non-irritant.

The results of the more sensitive IL-1α assay are documented in Table 2. SDS exposure resulted in a dose-dependent increase in IL-1α secretion, which was significant at all tested SDS concentrations. According to the IL-1α results, SDS is an irritant even at 0.2%. All OsCs alone did not induce IL-1α secretion and were considered non-irritants.

When each OsC was combined with each SDS concentration, a significant reduction in IL-1α secretion was observed, confirming the anti-irritant activity of the OsCs. Interestingly, using the lower MWs OsCs, OcC50 and OcC150, reduced the 0.2%- and 0.4%-SDS effect to such low levels that are defined as non-irritants. Using the higher MWs OsCs, OcC300 and TFF, the rescue effect was slightly reduced. While still very significant, in their presence only the 0.2% SDS could be define as a non-irritant.

This study documents the anti-irritant effect of OsCs against SDS-induced irritation, when OsCs are applied before the application of the irritant. This study suggests that unexpectedly the lower MW OsCs are superior in their protective, anti-irritant effect.

TABLE 2

| Test Agent | Average concentration of IL-1α (pg/mL) | Standard deviation | Results Skin irritant if IL1α (pg/mL) ≤ 50 pg/mL | Mean of viability (%) | Standard deviation |
|---|---|---|---|---|---|
| NC | 25.846 | 20.302 | NI | 100.00 | 7.81 |
| PC | 241.167 | 24.751 | I | 3.12 | 0.26 |
| 0.2% SDS | 128.18 | 23.298 | I | 74.75 | 37.07 |
| 0.4% SDS | 318.044 | 12.179 | I | 73.04 | 26.50 |
| 0.6% SDS | 450.641 | 10.189 | I | 19.21 | 24.54 |
| OcC50 | 0 | 12.504 | NI | 141.07 | 0.30 |
| OcC50 + 0.2% SDS | 16.044 | 19.286 | NI | 120.23 | 13.03 |
| OcC50 + 0.4% SDS | 38.829 | 20.137 | NI | 125.91 | 16.53 |
| OcC50 + 0.6% SDS | 114.365 | 26.744 | I | 108.11 | 12.04 |
| OcC 150 | 3.779 | 10.243 | NI | 75.72 | 34.05 |
| OcC150 + 0.2% SDS | 48.667 | 44.076 | NI | 96.58 | 14.27 |
| OcC150 + 0.4% SDS | 48.088 | 16.797 | NI | 99.63 | 36.41 |
| OcC150 + 0.6% SDS | 66.922 | 22.471 | I | 117.96 | 12.84 |
| OcC 300 | 0 | 5.042 | NI | 122.96 | 11.43 |
| OcC300 + 0.2% SDS | 23.145 | 13.062 | NI | 120.17 | 3.49 |
| OcC300 + 0.4% SDS | 127.707 | 105.573 | I | 89.40 | 4.38 |
| OcC300 + 0.6% SDS | 179.588 | 75.857 | I | 101.68 | 12.70 |
| TFF | 0 | 8.978 | NI | 115.23 | 20.62 |
| TFF + 0.2% SDS | 29.123 | 23.761 | NI | 143.69 | 4.92 |
| TFF + 0.4% SDS | 143.536 | 37.664 | I | 122.18 | 17.62 |
| TFF + 0.6% SDS | 245.049 | 94.906 | I | 125.77 | 16.44 |

Example 3: Retinol-Induced Irritation

A standard In Vitro Skin Irritation Test (SIT) was performed according to OCED guidelines. Test materials (30

μl) were topically applied onto three-dimensional human epidermal equivalents (EPI-200 from MatTek, Ashland, Mass.), n=3 tissues per treatment group. Test materials included a positive control irritant (5% sodium dodecyl sulfate, SDS), and a negative control (Phosphate Buffered Saline, PBS), retinol (0.3%, in (50% ethanol, 20% glycerin, 0.1% BHT, in PBS)), alone and combined with 1% of the OsCs of Table 1a. OsCs alone were also included. When using a combination, all test agents were mixed together before the topical application. After 60-minute exposure, the tissues were rinsed with PBS and were transferred to fresh medium. At 24 hours, media was collected for IL-1α analysis.

The results of this study are shown in Table 3. Values presented in Table 3 are calculated as total IL-1α secretion minus the basal level of IL-1α secretion (which is documented by the negative control).

As documented in Table 3, the 0.3% retinol significantly increased IL-1α secretion, documenting its known irritation activity. Combining the retinol with each of the OsCs tested resulted in reduced retinol-induced IL-1α secretion, and therefore reduced irritation of the combined material. Surprisingly, the highest MW OsC (OcC300) had the lowest anti-irritant effect, while the lowest MW OsC (OcC50) had the most significant anti-irritant effect.

This study documents the anti-irritant effect of OsCs against retinol-induced irritation, when OsCs are applied together with the irritant. This study demonstrates an unexpected correlation between the OsC's MW and their anti-irritant effect, with the lowest MW being most effective.

TABLE 3

| Test Compound | IL-1α (pg/mL) = Average IL1α (pg/mL) treated tissue minus Average IL1α (pg/mL) negative control | SDev |
|---|---|---|
| NC | 38.935 | 21.097 |
| PC | 129.764 | 40.385 |
| Retinol 0.3% | 98.301 | 47.597 |
| Retinol + TFF | 69.244 | 27.134 |
| Retinol + OcC 50 | 47.845 | 4.313 |
| Retinol + OcC 150 | 82.902 | 15.943 |
| Retinol + OcC300 | 104.992 | 15.133 |

Example 4: Skin Retention

Carbon powder was used to evaluate the retention ability of different OsCs on human skin. Carbon powder alone cannot be retained on skin. When mixed with water, the suspension is retained on the skin until it dries, and then the carbon powder flakes off.

Carbon powder was mixed with water, applied to leg skin, and let dry for 10 minutes. At that point the suspension was slightly moist and still retained on the skin. The treated sites were then covered with the four different OsCs described in Table 1a or remained uncovered, and let dry for 10 minutes. The retaining of the carbon powder (black marks) on the skin was documented at different time points by photography. The study was repeated three times. During the study period the skin was exposed to regular showers (soap, running water, at least daily), to sweating (e.g., exercise) and to cloth friction (e.g., gym pants and socks). The results of these studies are documented in Table 4.

TABLE 4

| | OsC | OcC50 | OcC150 | OcC300 | No OsC |
|---|---|---|---|---|---|
| Time 0 | ++++ | ++++ | ++++ | ++++ | ++++ |
| 10 min | ++++ | ++++ | ++++ | ++++ | − |
| 12 hr | +++ | +++ | +++ | +++ | − |
| 24 hr | +++ | +++ | +++ | +++ | − |
| 48 hr | ++ | ++ | ++ | ++ | − |
| 72 hr | + | + | + | + | − |
| 96 hr | +/− | +/− | +/− | +/− | − |

++++ Very strong black color
+++ strong black color
++ medium intensity black color
+ light black color
+/− faint but clearly visible black color
− No visible black color These results document the long-lasting retention effect of inventive compositions containing low molecular weight OsCs. The active agent may be retained on the skin for a prolonged time, e.g., at least about 96 hr, or at least for a longer period of time than what would be provided by the same composition that lacks the OsC. These results also document that the molecular weight of the originating chitosan does not affect the retention ability of the OsC. Both smaller and larger OsCs were similarly retained on the skin.

Example 5: Preparation of OsC Gel Formulations

OsCs can be used as powders, or can be prepared as liquid samples (suspensions), when the powders are suspended (e.g. in water or phosphate buffer or other aqueous solutions) to make e.g., 10-100 mg/mL (1-10% w/v) stock suspensions. The suspensions may be mixed (e.g., vortexed) for e.g., 1-10 minutes, while heated as needed. The resulting homogenized solutions of the OsCs may be directly used in the formulations, or they may be used in the formulation as dry powders.

Representative gel formulations are set forth in Table 5. A preservative (e.g., PHENONIP® adnphenoxyethanol), and/or a chelating agent (e.g., disodium EDTA), and/or a humectant (e.g., glycerin) may beadded first to the OsC (which is in a liquid form or a powder suspended in liquid, e.g., water). At this step it is also possible to further add to the mixture oil-soluble silicones, emollients, viscosity builders or emulsifiers (e.g., cyclomethicone, dimethicone, polysorbate 20, aluminum starch octyl succinate, sucrose cocoate, PEG-6 capric/caprylic triglycerides). In some embodiments, a second mixture of an appropriate thickener(s) (or OsC could serve, sometimes, as its own thickener), along with an anti-oxidant (e.g., BHT), may be prepared. The two mixtures may then be combined and mixed until homogeneity. Other anti-oxidants (e.g., ascorbic acid, sodium ascorbyl phosphate, lactoferrin, or tocopherol) may then be added to the combined mix and evenly mixed to form the resulting gel.

TABLE 5

| CTFA name | % W/W | % W/W | % W/W | % W/W | % W/W | % W/W | % W/W | % W/W | Average standard ranges |
|---|---|---|---|---|---|---|---|---|---|
| OsC 0.1-5% (liquid) | 85.8 | 88 | 94 | 90 | 94.9 | 95 | | | 0-100 |
| OsC (powder) | | | | | | | 1.0 | 5.0 | 0-10 |
| Deionized water | Up to 100 | Up to 100 | Up to 100 | Up to 100 | Up to 100 | Up to 100 | Up to 100 | Up to 100 | 0-100 |
| Phenoxyethanol | 0.75 | 0.75 | 0.75 | 0.75 | 0.75 | | 1.0 | 1.0 | 0-5 |
| Glycerin | 2.5 | 2.5 | | | | | | | 0-5 |
| Cyclomethicone | 2.0 | | | | | | | | 0-5 |
| Aluminum Starch Ocetyl Succinate | 0.75 | | | | | | | | 0-5 |
| Sucrose Cocoate | 1.0 | 1.0 | | | | | | | 0-5 |
| PEG-6 Capric/Caprylic Triglycerides | 3.0 | 3.0 | | | | | | | 0-5 |
| Disodium EDTA | 0.1 | 0.1 | | | 0.05 | | 0.05 | 0.05 | 0-1 |
| Polyacrylamine/Laureth-7/$C_{13-14}$ Isoparaffin | 2.5 | 2.75 | 2.9 | 2.9 | 3.2 | | 3.0 | | 0-5 |
| Ascorbic Acid | | 0.01 | | | | | | | 0-1 |
| Butylated Hydroxytoluene | | 0.1 | 0.01 | 0.05 | 0.05 | 0.1 | 0.05 | 0.05 | 0-1 |
| Polysorbate 20 | | 0.5 | | | | | | | 0-2 |
| Thickener (or OsC) | | | | | | 3.5 | | 3.0 | 0-6 |
| Other cosmetic or therapeutic agents | 1 | 0.25 | | 5 | | | 2.5 | | 0-10 |

Example 6: Preparation of OsC Oil-in-Water Formulations

Table 6 sets forth two representative examples of oil-in-water formulations. The OsCs can be prepared as in example 5. The ingredients of the lipid phase may be combined and mixed at about 50-85° C., and then cooled to about 40-60° C. In a separate vessel, the thickener may be slowly combined with the aqueous OsC or the powdery OsC reconstituted in water or an aqueous solution. After mixing for e.g., about ten minutes and heating when needed, the rest of the aqueous phase ingredients may be added and mixed, and then heated to about the lowest possible temperature of the lipid phase. The two phases can then be combined, mixed for e.g. for about ten minutes, and cooled to room temperature. The additional agents may be combined into both phases or after their mixing.

TABLE 6

| Phase | CTFA Name | % W/W | % W/W | Average standard ranges |
|---|---|---|---|---|
| OIL | Cetearyl Glucoside | 1.4 | 1.4 | 0.1-2.8 |
| | C12-15 Alkyl Benzoate | 4.0 | 4.0 | 1-6 |
| | Octyl Hydroxystearate | 1.0 | 1.0 | 0-5 |
| | Dimethicone | 1.0 | 1.0 | 0-5 |
| | Cyclomethicone | 1.0 | 1.0 | 0-5 |
| | Thickener (or OsC) | 2.5 | 2.5 | 0-4 |
| | Butylated Hydroxytoluene | 0.1 | 0.1 | 0-0.5 |
| | Octyl Methoxycinnamate | 6.0 | 6.0 | 0-10 |
| | Vitamin E acetate | 0.5 | 0.5 | 0-0.5 |
| | Tocopherol Acetate | 0.5 | 0.5 | 0-0.5 |
| | Other cosmetic or therapeutic agents | 0 | 0.25 | 0-10 |
| AQUEOUS | Glycerin | 3.0 | 3.0 | 0-20 |
| | D-Pathenol | 0.5 | 0.5 | 0-5 |
| | Disodium EDTA | 0.1 | 0.1 | 0.01-1 |

TABLE 6-continued

| Phase | CTFA Name | % W/W | % W/W | Average standard ranges |
|---|---|---|---|---|
| | Phenoxyethanol | 0.7 | 0.3 | 0-1 |
| | Thickener (or OsC) | 0.35 | 0.3 | 0-3 |
| | Deionized Water | Up to 100 | Up to 100 | 50-80 |
| | OsC in liquid form | | 75 | 0.001-90 |
| | OsC in powder form | 1.0 | | 0.001-20 |
| | Other cosmetic or therapeutic agents | 0 | 2 | 0-10 |

Example 7: Preparation of Water-in-Oil Formulations

Table 7 sets forth two representative examples of water-in-oil formulations. The OsCs can be prepared as in example 5. The emollients (e.g. mineral oil) may be melted, and the other oil phase ingredients may be added, followed by heating e.g. to about 75° C., to achieve homogeneity. The aqueous phase ingredients may be mixed separately and warmed to the lowest possible temperature of the liquid oil phase (while retaining of biological activity of the natural extract), followed by combining the two mixtures with stirring until it is congealed. The additional agents may be combined into both phases or after their mixing.

TABLE 6

| Phase | CTFA Name | % W/W | % W/W | Average standard ranges |
|---|---|---|---|---|
| OIL | Mineral Oil | 25.0 | 25.0 | 40-80 |
| | Sorbitan Monooleate | 5.0 | 5.0 | 1-6 |
| | Stearyl Alcohol | 25.0 | 25.0 | 20-60 |

TABLE 6-continued

| Phase | CTFA Name | % W/W | % W/W | Average standard ranges |
|---|---|---|---|---|
| | Dimethicone | 1.0 | 1.0 | 1-5 |
| | Cetyl Alcohol | 2.0 | 2.0 | 0.1-10 |
| | Thickener (or OsC) | 3.0 | 3.0 | 0-10 |
| | Parsol MCX | 3.0 | 3.0 | 0-10 |
| | Vitamin E acetate | 0.5 | 0.5 | 0.01-0.5 |
| AQUEOUS | Glycerin | 3.0 | 3.0 | 0-20 |
| | Phenoxyethanol | 0.7 | 0.7 | 0.01-1 |
| | Deionized Water | Up to 100 | Up to 100 | 20-45 |
| | OsC in liquid form | | 31.55 | 20-45 |
| | OsC in powder form | 1.0 | 0 | 0-10 |
| | Other active agents | 0 | 0.25 | 0-1 |

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A topical composition for delivery of an active agent to keratinous tissue, comprising a low molecular weight chitosan that is covalently modified with octane sulfonic acid groups which are attached to the chitosan via sulfonamide linkages (OsC), an effective amount of an active agent that causes skin irritation, and a pharmaceutically acceptable carrier, wherein the chitosan has a molecular weight of about 50 kilodaltons (kD), and wherein the active agent is present in an amount of at least about 0.6% W/V, based on the total weight of the composition.

2. The topical composition of claim 1, which is anhydrous.

3. The topical composition of claim 1, wherein the carrier is aqueous.

4. The topical composition of claim 1, wherein the carrier is multi-phasic.

5. The topical composition of claim 4, which is an emulsion.

6. The topical composition of claim 5, wherein the emulsion is a water-in-oil emulsion or an oil-in-water emulsion.

7. The topical composition of claim 1, wherein the active agent is a pharmaceutical active agent or a cosmetic active agent.

8. The topical composition of claim 7, wherein the pharmaceutical active agent is selected from the group consisting of retinoids, anti-bacterial agents, anti-viral agents, anti-parasitic agents, anti-wart agents, anti-fungal agents, anti-inflammatory agents, antibiotics, antiseptics, local anaesthetics, pharmaceutically active peptides, actinic keratosis treatments, rosacea treatments, psoriasis treatments, wound treatments, analgesics, acne therapeutic agents, and rosacea therapeutic agents.

9. The topical composition of claim 8, wherein the retinoid is selected from the group consisting of retinol, retinoic acid, retinaldehyde, esters of retinol or of retinoic acid, and synthetic retinoids.

10. The topical composition of claim 9, wherein the retinoid is retinol.

11. The topical composition of claim 9, wherein the retinoid is retinyl palmitate.

12. The topical composition of claim 9, wherein the retinoid is tocopheryl-retinoate, adapalene, bexarotene, tazarotene, all trans-retinol, 13-cis-retinoic acid, 9-cis-retinoic acid, or acitretin.

13. The topical composition of claim 8, wherein the effective amount of the retinoid is from about 0.6 to about 5% W/V, based on the total weight of the composition.

14. The topical composition of claim 7, wherein the cosmetic active agent is selected from the group consisting of sunscreen agents, anti-aging agents, vitamins and moisturizing agents.

15. The topical composition of claim 14, wherein the sunscreen agent is selected from the group consisting of octocrylene, octyl methoxycinnamate, homosalate, octisalate, octinoxate, avobenzone, and oxybenzone, and combinations of two or more thereof.

16. The topical composition of claim 1, wherein OsC is present in an amount of about 0.0001% W/V to about 5% W/V, based on the total weight of the composition.

17. The topical composition of claim 1, wherein OsC is present in an amount of about 0.001% W/V to about 3% W/V, based on the total weight of the composition.

18. The topical composition of claim 1, wherein OsC is present in an amount of about 0.5% W/V to about 2% W/V, based on the total weight of the composition.

19. A method of treating keratinous tissue comprising applying the topical composition of claim 1 to the keratinous tissue.

20. The method of claim 19, wherein the keratinous tissue is skin or scalp.

* * * * *